United States Patent [19]

Kadaba

[11] Patent Number: 4,820,721
[45] Date of Patent: Apr. 11, 1989

[54] 1-ARYL-5-(2-OXO-1-PYRROLIDINYL)-1,2,3-TRIAZOLINES AS NOVEL ANTICONVULSANTS

[76] Inventor: Pankaja K. Kadaba, 3411 Brookhaven Dr., Lexington, Ky. 40502

[21] Appl. No.: 180,163

[22] Filed: Apr. 11, 1988

[51] Int. Cl.$^4$ .................. A61K 31/41; C07D 249/06
[52] U.S. Cl. ................................ 514/359; 548/255
[58] Field of Search ................ 548/255; 514/359, 424

[56] References Cited

U.S. PATENT DOCUMENTS

| | | | |
|---|---|---|---|
| 3,470,196 | 9/1969 | Harvey | 260/308 |
| 3,965,074 | 6/1976 | Claussen et al. | 260/77.5 R |
| 4,013,441 | 3/1977 | Bianchetti et al. | 71/92 |
| 4,148,803 | 4/1979 | Wehrmeister | 260/308 A |
| 4,511,572 | 4/1985 | Kadaba | 514/340 |
| 4,610,994 | 9/1986 | Kadaba | 514/340 |
| 4,618,681 | 10/1986 | Kadaba | 546/276 |
| 4,689,334 | 8/1987 | Kadaba | 514/340 |

OTHER PUBLICATIONS

Kadaba, Pankaja K., "Permanganate Oxidation of 1,2,3-Triazolines Using Phase-Transfer Catalysis. Electronic and Steric Effects", Journal f. prakt. Chemie, Band 324, Heft 5, 1982, S. 857–864.
Kadaba, "Synthesis, International Journal of Methods in Synthetic Org. Chem.", No. 2, Feb. 1973, pp. 71–84.
Kadaba, "Tetrahedron", vol. 25, pp. 3053–3066, 1969.
Kadaba, "Jour. of Heterocyclic Chem.", vol. 6, 1969, pp. 587–589.
Kadaba, "J. Heterocylic Chem.", vol. 4, 1967, p. 301–304.
Kadaba, "Tetrahedron", 1966, vol. 22, pp. 2453–2460.
Kadaba, "J. of Org. Chem", 1961, vol. 26, pp. 2331–2335.
Kadaba, Pestic Sci., 1974, 5, 255–258.
Kadaba, Jour. of Pharmaceutical Science, vol. 59, No. 8, 1970, pp. 1190–1191.
Kadaba, "Synthesis", 1978, pp. 694–695.
Kadaba, J. Het. Chem., vol. 12, 1975, 143–146.
Kadaba, J. Het. Chem., vol. 13, 1976, 1153–4.
Kadaba, Heterocycles, 9, 243, 1978.

*Primary Examiner*—Glennon H. Hollrah
*Assistant Examiner*—Peter G. O'Sullivan
*Attorney, Agent, or Firm*—Lowe, Price, LeBlanc, Becker & Shur

[57] ABSTRACT

Anticonvulsant compounds are of the formula:

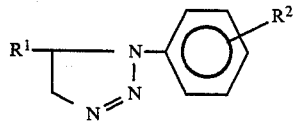

wherein $R^1$ is 2-oxo-1-pyrrolidinyl, and $R^2$ is hydrogen or p-chloro. They are prepared by the reaction of a phenyl azide with N-vinylpyrrolidinone.

9 Claims, No Drawings

1-ARYL-5-(2-OXO-1-PYRROLIDINYL)-1,2,3-TRIAZOLINES AS NOVEL ANTICONVULSANTS

TECHNICAL FIELD

This invention relates to novel, new and previously unknown, 2-oxo-1-pyrrolidinyl substituted 1,2,3-triazolines, their methods of preparation, and compositions for their use as a novel class of anticonvulsant drugs in the treatment of convulsive disorders.

BACKGROUND ART

N-Vinyl-2-pyrrolidinone (NVP) is the monomer of polyvinylpyrrolidinone (PVP). It has a unique N-(exocyclic vinyl)-lactam structure and is an example of N-vinylamide or enamide, just as N-vinylpyrrolidine is an example of N-vinylamine or enamine.

The olefinic bonds are typical dipolarophiles that undergo 1,3-dipolar cycloadditions with octetstabilized 1,3-dipoles such as organic azides to yield five-membered nitrogen-heterocycles, the Δ²-1,2,3-triazolines (4,5-dihydro-1H-1,2,3-triazoles) (Huisgen, et al, 1964; Huisgen, 1963; Kadaba et al, 1984). The literature abounds in cycloaddition reactions to the olefinic bond of enamines, but there is no record of any studies on cycloadditions to enamides. This invention describes for the first time the 1,3-cycloaddition reaction of a phenyl azide and a p-chlorophenyl azide with NVP and the synthesis and anticonvulsant activity of 1-aryl-5-(2-oxo-1-pyrrolidinyl)-1,2,3-triazolines.

DISCLOSURE OF THE INVENTION

One object of the present invention is to provide new 1-aryl-5-(2-oxo-1-pyrrolidinyl)-1,2,3-triazolines and a unique method for their preparation.

A further object of the present invention is to provide anticonvulsant compositions containing as the essential ingredient certain 1-aryl-5-(2-oxo-1-pyrrolidinyl)-1,2,3-triazolines and use of these triazolines as antiepileptic drugs in the treatment of convulsive disorders such as epilepsy.

This invention provides new triazoline compounds which are useful as anticonvulsant drugs. These compounds may be characterized by the following general formulae:

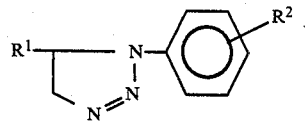

wherein $R^1$ is 2-oxo-1-pyrrolidinyl, and $R^2$ is hydrogen or p-chloro.

BEST MODE FOR CARRYING OUT THE INVENTION

As indicated above, this invention relates to certain 1,2,3-triazolines which are useful as anticonvulsants in mammals including humans. The triazolines of this invention are to be named as 1,2,3-triazolines or 4,5-dihydro-1H-1,2,3-triazoles. The triazolines of this invention are substituted in the 5-position by 2-oxo-1-pyrrolidinyl group and in the 1-position by an aryl group, which may also contain substituents. The triazoline compounds of this invention have potent anticonvulsant activity as antiepileptic drugs in the treatment of convulsive disorders such as petit mal (absence seizures), grand mal (major motor) seizures and partial seizures, both simple and complex partial.

In one aspect of the present invention, new compounds are provided which have anticonvulsant activity and which are of the following general formulae:

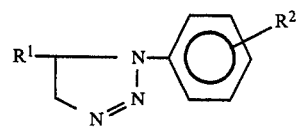

In the above formulae, $R^1$ is 2-oxo-1-pyrrolidinyl and $R^2$ is hydrogen or p-chloro.

In a further aspect of the present invention, a new method is described for the preparation of the 2-oxo-1-pyrrolidinyl substituted 1,2,3-triazolines. There is further provided by this invention, methods for administration of the anticonvulsant composition to mammals including animals and humans.

The compounds of the invention are prepared by the reaction of substantially equimolar amounts of NVP and an aryl azide, in the absence of solvent, for 3–6 weeks at room temperature. This reaction yields the hitherto unknown 1-aryl-5-(2-oxo-1-pyrrolidinyl)-1,2,3-triazolines as stable, crystalline products. The reaction proceeds according to Equation I as follows:

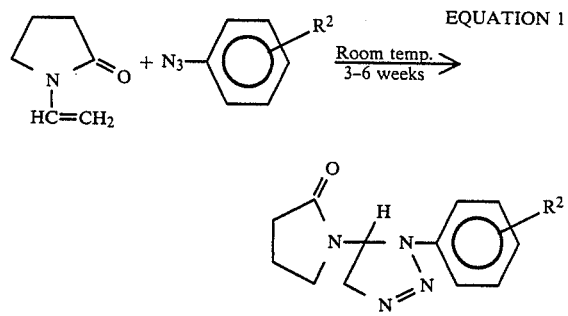

EQUATION 1

The reaction products are characterized and identified as 1,2,3-triazolines by their melting points, elemental analysis, and NMR spectra. Both triazoline compounds, in addition to the chemical shifts arising from the 5-(2-oxo-1-pyrrolidinyl) group, reveal two sets of multiplets with eight and four peaks respectively in the 4.3–4.4 δ and 6.3–6.8 δ region, an ABX pattern that is characteristic of 1,2,3-triazoline structures bearing two protons at the C-4 position and one proton at the asymmetric C-5 carbon.

The newly synthesized 1-aryl-5-(2-oxo-1-pyrrolidinyl)-1,2,3-triazolines exhibit good anticonvulsant activity in the subcutaneous pentylenetetrazole (Metrazole) seizure threshold (scMet) test and the maximal electro-shock seizure (MES) test. The melting points and anticonvulsant activity data of the new triazolines are reported in the Table.

The potency of the triazoline compounds range between moderate to good potency. They afford protection in both the scMet and MES seizure models. The 1-p-chlorophenyl-5-(2-oxo-1-pyrrolidinyl)-1,2,3-triazoline is active in the 100 mg/kg dose and the 1-phenyl-5-(2-oxo-1-pyrrolidinyl)-1,2,3-triazoline is active in the 300 mg/kg dose. The compounds do not exhibit significant signs of neurological deficit at their effective dose levels.

The anticonvulsant activity was evaluated by subjecting male albino mice to the MES test and the scMet test. The maximal electroshock seizure test (MES) was performed according to the method of Swinyard et al (J. Pharmacol. Exp. Ther. 106, 319, 1952), and abolition of the hind limb tonic extensor component of the maximal seizures was defined as protection. In the subcutaneous pentylenetetrazole seizure threshold test (scMet), 85 mg/kg of pentylenetetrazol was administered as a 0.5% solution subcutaneously in the posterior midline, and failure to observe even a threshold seizure (a single episode of clonic spasms of at least 5-s duration) was defined as protection.

Neurotoxicity was evaluated by the rotorod ataxia test (Dunham et al, J. Am. Pharm. Assoc. Sci. Ed., 46, 208, 1957). The animal was placed on a wooden rod of 2.8-cm diameter rotating at 6 rpm. Normal mice can remain on a rod rotating at this speed indefinitely. Neurologic toxicity was defined as the failure of the animal to remain on the rod for 1 min and was expressed as number of animals exhibiting toxicity/number of animals tested or as percent of animals showing toxicity.

The anticonvulsant compounds of the present invention may be administered to animals or humans at doses ranging from about 25 mg/kg to about 300 mg/kg. Preferred levels of administration range from about 25 mg/kg up to 100 mg/kg. The active ingredients or compounds of this invention may be administered in any desired form by injection or in the oral form. Conventional adjuvants and carriers may be employed in combination with about 0.001 to 2.0 wt% of the active ingredient. Thus the anticonvulsant compositions of this invention may be administered in pill form or by injection.

The following examples are presented to illustrate the invention but it is not to be considered as limited thereto. Parts are by weight unless otherwise indicated.

EXAMPLE 1

Using the reaction of Equation 1 described above, involving the reaction of p-chlorophenyl azide with N-vinylpyrrolidinone (NVP), compound 1, 1-p-chlorophenyl-5-(2-oxo-1-pyrrolidinyl)-1,2,3-triazoline, was prepared. Its melting point and yield are given in the Table. Also set forth in the Table are the anticonvulsant activity for the Phase I and Phase II tests.

EXAMPLE 2

Using the reaction of Equation 1 described above, involving the reaction of phenyl azide with N-vinylpyrrolidinone (NVP), compound 2, 1-phenyl-5-(2-oxo-1-pyrrolidinyl)-1,2,3-triazoline, was prepared. Its melting point and yield are given in the TAble. Also set forth is the anticonvulsant activity for Phase I.

those skilled in the art, the invention is not to e considered as limited thereto.

I claim:

1. A compound of the following formula:

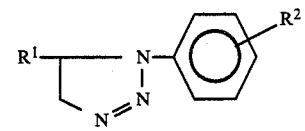

wherein $R^1$ is 2-oxo-1-pyrrolidinyl, and $R^2$ is hydrogen or p-chloro.

2. A compound according to claim 1 wherein $R^1$ is 2-oxo-1-pyrrolidinyl and $R^2$ is hydrogen.

3. A compound according to claim 1 wherein $R^1$ is 2-oxo-1-pyrrolidinyl, and $R^2$ is p-chloro.

4. An anticonvulsant composition comprising an effective amount of a compound selected from the group consisting of those of the formulae:

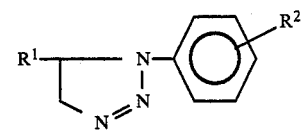

wherein $R^1$ is 2-oxo-1-pyrrolidinyl, and $R^2$ is hydrogen or p-chloro, and a pharmaceutically acceptable carrier or adjuvant.

5. A composition according to claim 4 wherein $R^1$ is 2-oxo-1-pyrrolidinyl and $R^2$ is hydrogen.

6. A composition according to claim 4 wherein $R^1$ is 2-oxo-1-pyrrolidinyl, and $R^2$ is p-chloro.

7. A composition according to claim 4 wherein a sufficient amount of the effective ingredient is contained in said composition to provide a dosage amount ranging from about 25 mg/kg to 300 mg/kg.

8. A method for the treatment of convulsive disorders in mammals which comprises administration thereto of an effective dosage amount of an anticonvulsant composition comprising an effective amount of a compound selected from the group consisting of those of the formulae:

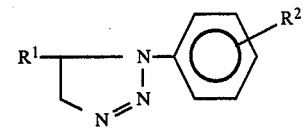

wherein $R^1$ is 2-oxo-1-pyrrolidinyl, and $R^2$ is hydrogen or p-chloro, and a pharmaceutically acceptable carrier or adjuvent.

9. A method according to claim 4 wherein the com-

TABLE

| Compound | m.p. °C. | Yield, % | Phase I | Phase II | |
|---|---|---|---|---|---|
| 1. 1-p-chlorophenyl-5-(2-oxo-1-pyrrolidinyl)-1,2,3-triazoline | 125–126 | 45 | 100 mg/kg | $ED_{50}MES$ $ED_{50}scMet$ $TD_{50}$ | 115.54 mg/kg 77.16 mg/kg 248.75 mg/kg |
| 2. 1-phenyl-5-(2-oxo-1-pyrrolidinyl)-1,2,3-triazoline | 119–120 | 22 | 300 mg/kg | | |

This invention has been described herein with reference to certain preferred embodiments. However, as obvious variations thereon will become apparent to position is administered in a dosage amount ranging from about 25 mg/kg to 300 mg/kg of body weight.

* * * * *